United States Patent [19]

Caspar et al.

[11] Patent Number: 4,612,932
[45] Date of Patent: Sep. 23, 1986

[54] MAGAZINE FOR C-SHAPED SCALP CLIPS

[75] Inventors: Wolfhard Caspar, Bad Homburg; Theodor Lutze, Balgheim; Karl-Ernst Kienzle, Immendingen, all of Fed. Rep. of Germany

[73] Assignee: Aesculap-Werke AG vormals Jetter & Scheerer, Tuttlingen, Fed. Rep. of Germany

[21] Appl. No.: 657,267

[22] Filed: Oct. 2, 1984

[30] Foreign Application Priority Data

Oct. 4, 1983 [DE] Fed. Rep. of Germany ....... 3335985

[51] Int. Cl.$^4$ ............................................. A61B 17/10
[52] U.S. Cl. .................................. 128/334 R; 128/325; 206/339; 206/340
[58] Field of Search ............... 128/334 R, 334 C, 325, 128/326, 337; 227/DIG. 1; 206/339, 340

[56] References Cited

U.S. PATENT DOCUMENTS

| 3,082,426 | 3/1963 | Miles | 128/334 R |
| 3,604,425 | 9/1971 | Le Roy | 128/325 |
| 4,206,863 | 6/1980 | Savino | 227/83 |
| 4,372,316 | 2/1983 | Blake et al. | 128/325 |
| 4,478,218 | 10/1984 | Mericle | 128/325 |

FOREIGN PATENT DOCUMENTS 3035390  6/1982  Fed. Rep. of Germany .

Primary Examiner—Michael H. Thaler
Attorney, Agent, or Firm—Kenway & Jenney

[57] ABSTRACT

A magazine for receiving C-shaped scalp clips having legs connected by a bridge and with facing clamping jaws at their free ends. In order to improve positioning of the scalp clips during displacement along the magazine, the scalp clips are arranged one behind the other in the magazine such that the free ends of one scalp clip rest against the bridge of the adjacent scalp clip, the scalp clips have laterally open recesses in their bridges or the regions where legs and bridge meet and the magazine has guide rails extending along its length and engaging in these recesses.

3 Claims, 4 Drawing Figures

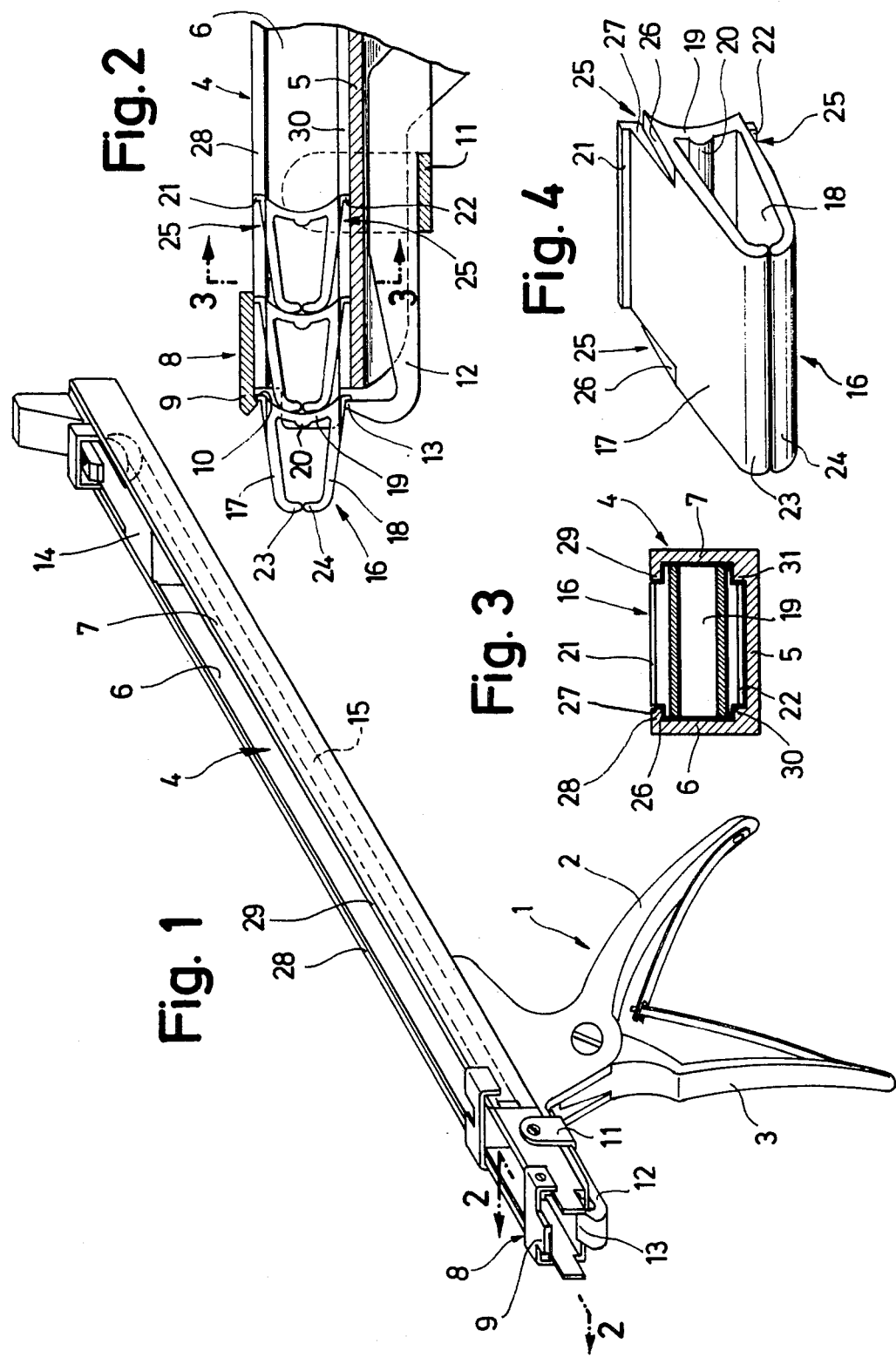

MAGAZINE FOR C-SHAPED SCALP CLIPS

The invention relates to a magazine for receiving C-shaped scalp clips having legs connected via a bridge and with facing clamping jaws at their free ends.

A magazine of this type for scalp clips is already known. The scalp clips are held in a circular magazine which gradually turns to bring the various clips into position for application one after the other (German Pat. No. 30 35 390).

A construction of this type is rather complicated as the magazine itself must be moved. The use of a stationary magazine and displacement of the scalp clips within the magazine is, however, thwarted by the fact that the scalp clips have an extremely complicated outer shape and cannot therefore be transported with the desired accuracy.

For this reason, no use has previously been made, apart from the circular magazine described, of magazines having a supply of scalp clips and scalp clips have been applied individually with forceps-like instruments, into which a new scalp clip must be inserted by hand after each application (U.S. Pat. Ser. No. 3,604,425).

The object of the invention is to develop a magazine for scalp clips further such that scalp clips having an elaborate shape can be reliably guided in a stationary magazine.

This object is accomplished according to the invention, for a magazine of the type described at the outset, in that the scalp clips are arranged one behind the other in the magazine such that the free ends of one scalp clip rest against the bridge of the adjacent scalp clip and that the scalp clips have laterally open recesses in their bridges or the regions where legs and bridge meet and the magazine has guide rails extending along its length and engaging in these recesses.

Even when the scalp clips have an elaborate outer contour, the guide rails ensure that the scalp clips are guided in the magazine in an exactly predetermined orientation. The scalp clips abut against one another such that the following clips can push the front clips forward towards the open end of the magazine. A very simple construction of this type enables a large number of scalp clips to be disposed in the magazine and displaced along the magazine without any risk of tilting or faulty orientation occurring.

It is advantageous for the guide rails to be formed by the inwardly bent edges of the U-shaped magazine as the guide rails are then particularly easy to produce.

It is also favourable for a step forming a guide rail to be disposed at the point where the bottom of the magazine and the side walls meet so that it projects into the cross section of the magazine. In particular, the combination of such a guide rail with the inwardly bent upper edge of the magazine ensures that the scalp clips are guided in the magazine so as to be parallel in an absolutely reliable manner.

This applies all the more when, in a preferred embodiment, the guide rails and the surfaces of the recesses abutting thereon extend parallel to the direction of feed of the scalp clips in the magazine.

In the preferred embodiment of the invention, the bridges of the scalp clips are concave in shape and the following scalp clip has a convex cross section in the region of its free legs so that the convex portions of the following scalp clips engage in the concave bridge of each preceding scalp clip. In this way, the following scalp clip is centered, i.e. the alignment effected by the guide rails is also considerably aided by this construction.

The following description of a preferred embodiment of the invention serves to explain the invention in more detail, in conjunction with the drawings.

FIG. 1 is a perspective view of an applicator for scalp clips;

FIG. 2 is a sectional view along line 2—2 in FIG. 1;

FIG. 3 is a sectional view along line 3—3 in FIG. 2 and

FIG. 4 is an enlarged perspective view of a scalp clip.

The applicator illustrated in FIG. 1 comprises a handle part 1 having two branch elements 2 and 3 which are pivotable towards one another. Branch element 2 is rigidly secured to the grip part 1 which bears an elongated magazine 4 with a U-shaped cross section, a bottom 5 and two side walls 6 and 7 arranged at right angles to the bottom. The magazine 4 is open at its front end and bears, in this region, a U-shaped bracket 8 which spans the open upper side. This bracket has a downwardly projecting edge 10 at its front end, on a projecting tongue 9. On the underside of the magazine, a U-shaped bracket 11 is mounted on the handle part 1 for pivoting movement about a horizontal axis extending transversely to the longitudinal direction of the magazine. Attached to this bracket 11 is a lower applying instrument 12 having an edge 13 lying opposite the edge 10 and projecting upwardly into the cross section of the magazine. The applying instrument 12 can be pivoted by means of the movable branch element 3. Manufacture of the appropriate mechanism is not a problem for the person skilled in the art and for this reason it is not specifically shown in the drawings.

A slider 14 is mounted in the magazine 4 for longitudinal displacement. This slider may be displaced towards the front open end of the magazine by means of a spirally wound leaf spring 15 which is mounted in the interior of the slider.

The magazine accommodates a large number of scalp clips 16. Their construction is shown in FIGS. 2 and 4. Each scalp clip 16 has two plane legs 17 and 18 joined at one end by a concave bridge 19 which forms an acute angle at its junction with the legs. This bridge 19 has, in the centre between the two legs 17 and 18, a bead-like bulge 20 extending transversely to the direction of the clips. This bulge 20 stabilizes the bridge and, when the clip is bent open, stabilizes the bending force on the bridge regions to both sides of this bulge.

At the ends of the two legs 17 and 18 towards the bridge these legs each have an edge 21 or 22 projecting at right angles, the function of which will be explained later on. At their free ends, the two legs are curved towards the centre and end in facing clamping jaws 23 or 24. The legs 17 and 18 converge towards their free ends and, in the region of these ends, the clip has a substantially convex cross sectional form due to the curved clamping jaws.

As clearly shown in FIGS. 3 and 4, recesses 25 are worked into the legs 17 and 18 on both sides in the regions where legs and bridge meet. These recesses are defined by two application surfaces 26 and 27 arranged at right angles to one another. The application surfaces 26 which extend in the direction of the legs and are arranged on opposite sides of the scalp clip are parallel to one another. The application surfaces 27 arranged at right angles thereto are also parallel to one another on opposite sides of a leg so that steplike recesses result in the rearward region of each clip, when seen from the front of the clip, as clearly shown by the illustration in FIG. 3.

The cross section of the magazine is essentially rectangular but the side walls 6 and 7 are bent slightly inwards at their upper edges to form the guide rails 28 and 29 which project into the cross section and extend along the length of the magazine. A step 30 or 31 is formed at the point where the bottom 5 meets each of the side walls 6 and 7, these steps projecting into the cross section of the magazine. They also form guide rails extending in the longitudinal direction of the magazine (FIG. 3). Their dimensions are selected such that when a scalp clip is inserted into the magazine its substantially horizontal application surfaces 26 rest againstthe underside of the guide rails 28 and 29 and on the upper side of steps 30 and 31 while the vertical application surfaces 27 of the scalp clip rest against the front edges of guide rails 28 and 29 and on the vertical limits of steps 30 and 31, as clearly shown in the illustration of FIG. 3. In this way, the scalp clips are reliably guided along the guide rails 28 and 29 and the steps 30 and 31 so that the scalp clips cannot twist or tilt when displaced along the magazine. The scalp clips are thereby guided merely in the region near to their bridges. They are not in contact at all with the magazine in the region near to their clampingjaws since the clamping jaws are inclined towards one another, as clearly shown by the illustration in FIG. 2. However, the scalp clips are also centered in the region of their clamping jaws. When.the scalp clips are inserted into the magazine one after the other the concave region of the clamping jaws of one scalp clip engages in the convex bridge of the preceding scalp clip and is centered therein. This is also clearly illustrated in FIG. 2.

The scalp clips are therefore reliably positioned and guided along the magazine, firstly by the guide rails and steps and the recesses in the scalp clip cooperating therewith and, secondly, by the region of the clamping jaws being centered in the adjacent scalp clip.

The inserted scalp clips are pushed forward towards the open end of the magazine by the slider 14. The leading scalp clip thereby comes to rest against the edge 10 and the edge 13 with its edges 21 and 22 so that no further forward movement is possible (FIG. 2). By pivoting the lower applying instrument 12, the edge 13 can be brought closer to the edge 10 so that the scalp clip is bent open by this movement. The clip can now be applied to the tissue such that the clamping jaws clamp the tissue firmly between them once the lower applying instrument 12 has been pivoted out of its applying position. Since the clip remains in a slightly opened position, due to the tissue clamped therebetween, the distance between the two edges 21 and 22 is smaller and so the applying instrument can easily be withdrawn from the clip after application. The slider 14 then moves the entire row of scalp clips forwards until the next clip comes to rest against the edge 10 and the edge 13 with its edges 21 and 22.

The exact positioning of the scalp clip relative to the instruments is also of great importance because the scalp clips can then be bent open to an exactly defined degree and any overstressing which could ruin the scalp clips is thereby avoided. The application of the scal clips can also be repeated at will since it is always ensured that each scalp clip has exactly the same position relative to the applying instruments.

The manner in which the scalp clips are guided, as described above, also ensures that the scalp clips are moved forward in the magazine without any tilting or twisting and so no interruption occurs during operation.

In the embodiment illustrated, the recesses 25 are arranged on the upper and lower sides of the scalp clip. These recesses could, of course, be arranged on the side faces of the scalp clip instead. This would entail the guide rails being positioned accordingly so that they engage exactly in the recesses and can guide the scalp clips.

For the sake of completeness only, reference is made to the fact that protection is claimed not only for the design of the magazine but also for the design of the scalp clip itself. The inventive scalp clip and magazine are adapted to one another such that the scalp clips can be optimally guided in the magazine.

We claim:

1. In combination, C-shaped scalp clips and a magazine for receiving C-shaped scalp clips each of said scalp clips having legs connected via a bridge and with facing clamping jaws at their free ends, said scalp clips being arranged one behind the other in the magazine such that the free ends of one scalp clip rest against the bridge of the adjacent scalp clip, said scalp clips having laterally open recesses in their bridges including the regions where legs and bridge meet, said magazine having guide rails extending along its length and engaging in said recesses, and each said scalp clip having a bridge that is concave in shape and a convex cross section in the region of the free ends of its legs so that the convex portions of each following scalp clip engages the concave bridge of the preceding scalp clip.

2. The combination as defined in claim 1, wherein the guide rails are formed by the inwardly bent edges of the magazine which is of U-shaped cross section.

3. The combination as defined in claims 1 or 2, wherein a step forming a guide rail is disposed at the point where the bottom of the magazine and the side walls meet, said step projecting into the magazine cross section.

* * * * *